United States Patent [19]

Odawara et al.

[11] Patent Number: 5,387,581
[45] Date of Patent: Feb. 7, 1995

[54] PHARMACEUTICAL COMPOSITION OF ASPIRIN AND A BENZOTHIAZEPINE FOR INHIBITING PLATELET AGGREGATION

[75] Inventors: Akio Odawara, Tokyo; Yasuhiko Sasaki, Urawa; Sakae Murata, Kawagoe; Hiroshi Narita, Urawa, all of Japan

[73] Assignee: Tanabe Seiyaku Co. Ltd., Osaka, Japan

[21] Appl. No.: 35,895

[22] Filed: Mar. 23, 1993

Related U.S. Application Data

[63] Continuation of Ser. No. 748,965, Aug. 23, 1991, abandoned.

[30] Foreign Application Priority Data

Sep. 17, 1990 [JP] Japan .................. 2-243728
Sep. 17, 1990 [JP] Japan .................. 2-243729

[51] Int. Cl.6 .................. A61K 31/60; A61K 31/55; A61K 31/52
[52] U.S. Cl. .................. 514/165; 514/211; 514/264
[58] Field of Search .................. 514/211, 165

[56] References Cited

U.S. PATENT DOCUMENTS

| | | | |
|---|---|---|---|
| 4,567,175 | 1/1986 | Takeda et al. | 514/211 |
| 4,590,188 | 5/1986 | Takeda et al. | 514/211 |
| 4,594,342 | 6/1986 | Takeda et al. | 514/211 |
| 4,724,266 | 8/1988 | Satzinger et al. | 560/143 |
| 4,806,530 | 2/1989 | Langer | 514/161 |

FOREIGN PATENT DOCUMENTS 0214881 3/1987 European Pat. Off. .
0255141 2/1988 European Pat. Off. .

OTHER PUBLICATIONS

CA: 107(15) #134332w (1987).
CA: 108(13) #112510w Takeda (1988).
CA: 108(1) #6054y Morimoto (1988).
International Drug Directory 1990/1991, p. 1141.

Primary Examiner—Marianne M. Cintins
Assistant Examiner—T. J. Criares
Attorney, Agent, or Firm—Birch, Stewart, Kolasch & Birch

[57] ABSTRACT

There is disclosed a pharmaceutical composition for inhibiting the platelet aggregation comprising acetylsalicyclic acid or a pharmaceutically acceptable salt thereof and a 1,5-benzothiazepine derivative of the formula:

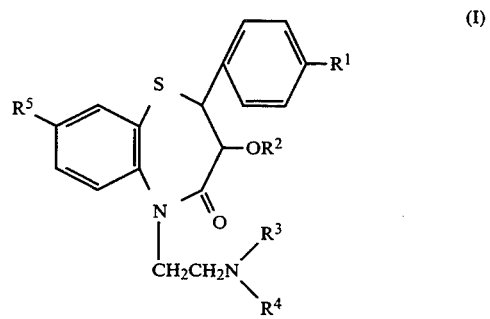

wherein $R^1$ is a lower alkyl group or a lower alkoxy group, $R^2$ is hydrogen atom or a lower alkanoyl group, $R^3$ is a lower alkyl group, $R^4$ is hydrogen atom or a lower alkyl group and $R^5$ is a lower alkyl group or a halogen atom, or a pharmaceutically acceptable salt thereof.

6 Claims, No Drawings

PHARMACEUTICAL COMPOSITION OF ASPIRIN AND A BENZOTHIAZEPINE FOR INHIBITING PLATELET AGGREGATION

This application is a continuation of application Ser. No. 07/748,965 filed on Aug. 23, 1991, now abandoned.

This invention relates to a pharmaceutical composition for inhibiting platelet aggregation.

It is known that 1,5-benzothiazepine derivatives such as 2-(4-methylphenyl)-3-hydroxy-5-[2-(dimethylamino)ethyl]-8-methyl-2,3-dihydro-1,5-benzothiazepin-4(5H)-one, 2-(4-methoxyphenyl)-3-hydroxy-5-[2-(dimethylamino)ethyl]-8-chloro-2,3-dihydro-1,5-benzothiazepin-4(5H)-one and the corresponding 3-acetoxy-compounds have an antihypertensive, coronary vasodilating and/or platelet aggregation-inhibiting activities (U.S. Pat. Nos. 4567175, 4590188 and 4594342 ). It is also known that acetylsalicylic acid is useful as the platelet aggregation inhibitor. However, this compound is apt to produce serious side effect in the gastrointestinal tract and in the kidneys.

Therefore, it is of decisive therapeutic importance to keep the dosage of the acetylsalicylic acid as low as possible.

As a result of the various investigations, the inventors of the present invention have now found that inhibitory effects on the platelet aggregation is enhanced in a synergistic manner by means of combined use of acetylsalicylic acid and the above-mentioned benzothiazepine derivatives, compared with either agent alone. Thus, according to the present invention, there is provided a pharmaceutical composition for inhibiting platelet aggregation which comprises acetylsalicylic acid or a pharmaceutically acceptable salt thereof and a 1,5-benzothiazepine derivative of the formula:

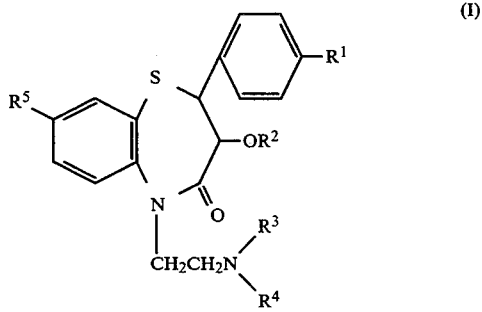

(I)

wherein $R^1$ is a lower alkyl group or a lower alkoxy group, $R^2$ is hydrogen atom or a lower alkanoyl group, $R^3$ is a lower alkyl group, $R^4$ is hydrogen atom or a lower alkyl group and $R^5$ is a lower alkyl group or a halogen atom, or a pharmaceutically acceptable salt thereof.

Example of the 1,5-benzothiazepine derivatives of the present invention may include the compounds of the formula (I), wherein $R^1$ is a lower alkyl group such as methyl, ethyl, propyl or butyl, or a lower alkoxy group such as methoxy, ethoxy, propoxy or butoxy, $R^2$ is hydrogen atom or a lower alkanoyl group such as acetyl, propionyl or butyryl, $R^3$ is a lower alkyl group such as methyl, ethyl, propyl or butyl, $R^4$ is hydrogen atom or a lower alkyl group such as methyl, ethyl, propyl or butyl, and $R^5$ is a lower alkyl group such as methyl, ethyl, propyl or butyl, or a halogen atom such as chlorine, bromine or fluorine. Among them, preferred compounds (I) are those wherein $R^1$ is methyl or methoxy, $R^2$ is hydrogen atom or acetyl, $R^3$ is methyl, $R^4$ is hydrogen atom or methyl, and $R^5$ is methyl or chlorine.

Since the 1,5-benzothiazepine derivatives (I) of the present invention has two asymmetric carbon atoms at 2-position and 3-position of benzothiazepine ring, there exist two kinds of stereoisomers [namely, cis- and trans-isomers] and four kinds of optical isomers [namely, (+)-cis-, (−)-cis-, (+)-trans- and (−)-trans-isomers]. The present invention is inclusive of either of these isomers and their mixtures.

The acetylsalicylic acid and 1,5-benzothiazepine derivatives (I) of the present invention can be used for medical use of either in free form or in the form of pharmaceutically acceptable salt thereof. Pharmaceutically acceptable salts of acetylsalicylic acid include, for example, sodium salt. On the other hand, pharmaceutically acceptable salts of the compound (I) include, for example, inorganic acid addition salt such as hydrochloride, hydrobromide, sulfate or phosphate, and organic acid addition salt such as oxalate, acetate, maleate, fumarate, tartrate and methanesulfonate.

A preferred weight ratio of acetylsalicylic acid or a pharmaceutically acceptable salt thereof to the 1,5-benzothiazepine derivative (I) or a pharmaceutically acceptable salt thereof is 0.3–40:1, especially 1–10:1.

A preferred dosage of the 1,5-benzothiazepine derivatives (I) or a pharmaceutically acceptable salt thereof is 5 to 60 mg, especially 10 to 30 mg, per day. On the other hand, a preferred dosage of acetylsalicylic acid or a pharmaceutically acceptable salt thereof is 20 to 200 mg, especially 30 to 100 mg, per day.

The composition of the present invention can be used by way of either oral administration or parenteral administration. In the case of oral administration, the composition of the present invention can be used as a pharmaceutical preparation together with a pharmaceutical carrier suitable for oral administration. The pharmaceutical carriers include, for example, conventional excipients, binders, disintegrators, lubricants such as starch, lactose, glucose, gelatin, sorbitol, tragacanth gum, polyvinylpyrrolidone, sugar, corn starch, polyethylene glycol, talc, potassium phosphate and magnesium stearate. Further, the dosage form may be a solid preparation such as tablets, pills, capsules, suppositories or it may also be a liquid preparation such as solutions, suspensions, emulsions. On the other hand, in the case of parenteral administration, the composition of the present invention may be preferably used as an injection, and as the pharmaceutical carrier for this purpose, for example, distilled water for injection, vegetable oil, propylene glycol, etc., can be suitably used. If required, dissolving agent, buffering agent, stabilizing agent, etc., may be also contained.

As described above, the pharmaceutical composition of the present invention has excellent inhibitory effects on the platelet aggregation, and therefore it can be effectively used for treatment of coronary or cerebrovascular thrombosis, peripheral vascular disease, platelet aggregation disorders and migraine.

EXPERIMENTAL EXAMPLE

Platelet aggregation-inhibiting Activity (Method)

Nine volumes of human blood were mixed with one volume of an aqueous 3.8% trisodium citrate solution, and the mixture was centrifuged to give platelet-rich plasma (hereinafter referred to as "PRP") as the supernatant solution. The bottom layer was further centrifuged to give platelet-poor plasma (hereinafter referred to as "PPP") as the supernatant solution. PRP was diluted with PPP so that the blood platelet count was $4 \times 10^5/mm^3$. Then, 175 μl of said diluted PRP were added to a mixture of 25 μl of a solution of the following test compound (A), (B), (C) or (D) and 25 μl of a solution of acetylsalicylic acid (E). After the mixture was stirred for 2 minutes at 37° C., 25 μl of a collagen solution [Biochem. Biophys. Acta, 186, page 254 (1969)] was added thereto, and the degree of platelet aggregation was estimated by the method of Born [Nature, 194, page 927 (1962)].

In the control group, a mixture of 175 μl of diluted PRP, 25 μl of a solution of the test compound (A), (B), (C), (D) or (E) and 25 μl of a physiological saline solution was tested. Further, as a non-medicated control group, a mixture of 175 μl of said diluted PRP and 50 μl of a physiological saline solution was used.

(Test compounds)

(A) (−)-cis-2-(4-methylphenyl)-3-acetoxy-5-[2-(dimethylamino)ethyl]-8-methyl-2,3-dihydro-1,5-benzothiazepin-4(5H)-one maleate ($R^1$, $R^3$, $R^4$ and $R^5$=methyl, $R^2$=acetyl.)

(B) (−)-cis-2-(4-methylphenyl)-3-hydroxy-5-[2-(methylamino)ethyl]-8-methyl-2,3-dihydro-1,5-benzothiazepin-4(5H)-one hydrochloride ½ $H_2O$ ($R^1$, $R^3$ and $R^5$=methyl, $R^2$ and $R^4$=hydrogen atom)

(C) (+)-cis-2-(4-methoxyphenyl)-3-acetoxy-5-[2-(dimethylamino)ethyl]-8-chloro-2,3-dihydro-1,5-benzothiazepin-4(5H)-one maleate ($R^1$=methoxy, $R^2$=acetyl, $R^3$ and $R^4$=methyl, $R^5$=chlorine.)

(D) (+)-cis-2-(4-methoxyphenyl)-3-hydroxy-5-[2-(dimethylamino)ethyl]-8-chloro-2,3-dihydro-1,5-benzothiazepin-4 (5H)-one ($R^1$=methoxy, $R^2$=hydrogen atom, $R^3$ and $R^4$=methyl, $R^5$=chlorine.)

(E) Acetylsalicylic acid (Result)

The results are shown in TABLE 1.

TABLE 1

|  | Concentration of test Compound(s) (μg/ml) | | | | | Platelet Aggregation |
|---|---|---|---|---|---|---|
|  | (A) | (B) | (C) | (D) | (E) | % |
| The present invention | 30 | — | — | — | 10 | 25 |
|  | — | 0.1 | — | — | 10 | 25 |
| Control | — | — | 30 | — | 10 | 20 |
|  | — | — | — | 10 | 10 | 19 |
|  | 30 | — | — | — | — | 75 |
|  | — | 0.1 | — | — | — | 63 |
|  | — | — | 30 | — | — | 73 |
|  | — | — | — | 10 | — | 58 |
|  | — | — | — | — | 10 | 74 |
| Non-medicated control | — | — | — | — | — | 74 |

What we claim is:

1. A pharmaceutical composition for inhibiting platelet aggregation, which comprises acetylsalicylic acid and (−)-cis-2-(4-methylphenyl)-3-acetoxy-5-[2-(dimethylamino)ethyl]-8-methyl-2,3-dihydro-1,5-benzothiazepin-4(5H)-one maleate, wherein the weight ratio of acetylsalicylic acid to (−)-cis-2-(4-methylphenyl)-3-acetoxy- 5-[2-(dimethylamino)ethyl]-8-methyl-2,3-dihydro-1,5-benzothiazepin-4(5H)-one maleate is 0.3–40:1.

2. The composition according to claim 1, wherein the weight ratio of acetylsalicylic acid to (−)-cis-2-(4-methylphenyl)-3-acetoxy-5-[2-(dimethylamino)ethyl]-8-methyl-2,3-dihydro-1,5-benzothiazepin-4(5H)-one maleate is 1–10:1.

3. The composition according to claim 1, wherein acetylsalicylic acid is present in an amount to provide a dosage level of 20 to 200 mg per day and (−)-cis-2-(4-methylphenyl)-3-acetoxy-5-[2-(dimethylamino)ethyl]-8-methyl-2,3-dihydro-1,5-benzothiazepin-4(5H)-one maleate is present in an amount to provide a dosage level of 5 to 60 mg per day.

4. The composition according to claim 1, wherein acetylsalicylic acid is present in an amount to provide a dosage level of 30 to 100 mg per day and (−)-cis-2-(4-methylphenyl)-3-acetoxy-5-[2-(dimethylamino)ethyl]-8-methyl-2,3-dihydro-1,5-benzothiazepin-4(5H)-one maleate is present in an amount to provide a dosage level of 10 to 30 mg per day.

5. The composition according to claim 2, wherein acetylsalicylic acid is present in an amount to provide a dosage level of 20 to 200 mg per day and (−)-cis-2-(4-methylphenyl)-3-acetoxy-5-[2-(dimethylamino)ethyl]-8-methyl-2,3-dihydro-1,5-benzothiazepin- 4(5H)-one maleate is present in an amount to provide a dosage level of 5 to 60 mg per day.

6. The composition according to claim 2, wherein acetylsalicylic acid is present in an amount to provide a dosage level of 30 to 100 mg per day and (−)-cis-2-(4-methylphenyl)-3-acetoxy-5-[2-(dimethylamino)ethyl]-8-methyl-2,3-dihydro-1,5-benzothiazepin-4(5H)-one maleate is present in an amount to provide a dosage level of 10 to 30 mg per day.

* * * * *